United States Patent [19]

Thornton et al.

[11] Patent Number: 4,584,413

[45] Date of Patent: Apr. 22, 1986

[54] PURIFICATION OF TERTIARY BUTYL HYDROPEROXIDE CONTAINING PRIMARY AND SECONDARY ALKYL HYDROPEROXIDE CONTAMINANTS

[75] Inventors: William B. Thornton, Woodlyn, Pa.; Alfred E. Borchert, Cherry Hill, N.J.

[73] Assignee: Atlantic Richfield Company, Los Angeles, Calif.

[21] Appl. No.: 531,979

[22] Filed: Sep. 14, 1983

[51] Int. Cl.$^4$ .......................................... C07C 179/025
[52] U.S. Cl. ..................................... 568/576; 568/569
[58] Field of Search ................ 568/571, 576, 385, 569

[56] References Cited

U.S. PATENT DOCUMENTS

| | | |
|---|---|---|
| 2,430,864 | 11/1947 | Farkas et al. ........................ 568/568 |
| 2,845,461 | 7/1958 | Winkler et al. ...................... 568/571 |
| 3,427,229 | 2/1969 | Herzog ................................ 549/541 |
| 3,445,523 | 5/1969 | Rosenthal et al. ................... 568/568 |
| 3,449,217 | 6/1969 | Harvey .................................... 203/6 |
| 3,773,687 | 11/1973 | Borchert et al. ..................... 568/559 |
| 3,864,216 | 2/1975 | Worrell et al. ......................... 203/49 |
| 4,408,083 | 10/1983 | Toyoura et al. ..................... 568/576 |

FOREIGN PATENT DOCUMENTS

| | | | |
|---|---|---|---|
| 1225645 | 11/1962 | Fed. Rep. of Germany ...... | 568/576 |
| 957952 | 5/1964 | United Kingdom . | |
| 1232709 | 5/1971 | United Kingdom . | |
| 1232710 | 5/1971 | United Kingdom . | |

OTHER PUBLICATIONS

Winkler et al., *Ind. Eng. Chem.*, vol. 53, No. 8, pp. 655–658, 1961.
Rieche et al., *Chemische Berichte*, 92, pp. 2239–2252, 1959.
Davies et al., *J. Chem. Soc.*, pp. 2204–2209, 1954.
Swern, ed., *Organic Peroxides*, vol. II, pp. 52–53, (1971), v. 2.

*Primary Examiner*—Natalie Trousof
*Assistant Examiner*—Bruce D. Gray
*Attorney, Agent, or Firm*—Michael S. Jarosz

[57] ABSTRACT

This invention relates to the purification of tertiary butyl hydroperoxide containing minor amounts of primary and secondary alkyl hydroperoxide contaminants obtained by the oxidation of isobutane by contacting the tertiary butyl hydroperoxide with at least about 2 milliequivalents per gram of total hydroperoxide present of a hydroxide or an oxide of an alkali metal or alkaline earth metal in aqueous solution and recovering the desired tertiary butyl hydroperoxide containing substantially reduced concentrations of primary and secondary alkyl hydroperoxide contaminants.

11 Claims, No Drawings

PURIFICATION OF TERTIARY BUTYL HYDROPEROXIDE CONTAINING PRIMARY AND SECONDARY ALKYL HYDROPEROXIDE CONTAMINANTS

BACKGROUND OF THE INVENTION

Tertiary butyl hydroperoxide, a well-known commercial chemical produced by the liquid phase oxidation of isobutane, is useful for various purposes, for example, as a chemical intermediate and as a free radical polymerization initiator for vinyl monomers. A typical process for the liquid phase oxidation of isobutane employing a molecular oxygen-containing gas is described in Winkler et al U.S. Pat. No. 2,845,461. Tertiary butyl hydroperoxide resulting from this process is produced in admixture with tertiary butyl alcohol, a by-product of the oxidation reaction, together with minor amounts of other oxidation products such as acetone, formic acid, other alcohols and esters of formic acid and the like, as well as primary and secondary alkyl hydroperoxide contaminants. The tertiary butyl hydroperoxide product can be separated from a majority of these by-products by fractional distillation as described in U.K. Pat. No. 1,232,709, wherein the distillation is effected in the presence of a diluent vapor, or is recovered as a bottom stream in a distillation process utilizing a reflux agent, as described in Herzog U.S. Pat. No. 3,427,229. A disadvantage encountered in distillations of isobutane oxidation mixtures is that there tends to occur significant decomposition of the tertiary butyl hydroperoxide, thereby contaminating the desired tertiary butyl hydroperoxide product with additional quantities of oxygen-containing decomposition products; hence, in an effort to avoid hydroperoxide decomposition, processes have been suggested whereby the distillation is carried out in the presence of a material which is capable of maintaining the effective pH of the liquid fraction during the distillation below about 9, and preferably below about 8, as disclosed in Harvey U.S. Pat. No.3,449,217.

It has been proposed in Farkas et al U.S. Pat. No. 2,430,864 to effect oxidation of certain cyclic hydrocarbons to produce saturated cyclic hydrocarbon hydroperoxides in the presence of a basic compound, thereby forming salts with acids which are produced during the oxidation, thus effectively removing acids which appear to be catalysts for the decomposition of peroxides. It has also been suggested by D. E. Winkler et al, Industrial Engineering Chemistry, 53, 655–658 (1961) to rinse the oxidation reactor employed in the oxidation of isobutane for the production of tertiary butyl hydroperoxide with a dilute solution of sodium pyrophosphate which serves as a neutralizer and metal ion scavenger.

In U.K. Pat. No. 1,232,710, dated Sept. 15, 1971, treatment of tertiary butyl hydroperoxide, obtained by the molecular oxygen-containing gas oxidation of isobutane, with from about 0.05 to about 1 milliequivalents of an inorganic base, organic amine, or basic ion exchange resin, per gram of hydroperoxide; i.e. an amount sufficient to avoid a highly alkaline pH which would cause the hydroperoxide to react; according to this patent, the product hydroperoxide preferably has a pH in water close to 7 for final storage, the function of the base being stated to be for removal of metal formate, t-butyl formate and formic acid. U.K. Pat. No. 957,952 discloses the hydrolysis of neutral impurities admixed with specified organic peroxides by contacting the peroxide with ammonia.

Rosenthal et al U.S. Pat. No. 3,445,523 discloses that organic hydroperoxide, illustratively tertiary butyl hydroperoxide, may be stabilized with an aqueous mixture of (1) sodium or potassium hydroxide and (2) sodium or potassium dihydrogen phosphate, the pH of the hydroxide and the aqueous mixture being in the range of between 7 and 8.

Still other methods of purification of organic peroxides described in the literature include precipitation from concentrated alkali, as described by A. G. Davies et al, J. Chem. Soc. page 2204–2209 (1954) or by derivatization with an appropriate reagent, as described by A. Rieche et al, Chem. Berichte, 92 beginning at page 2239 (1959). However, separation of tertiary butyl hydroperoxide from isomeric hydroperoxide contaminants is not specifically disclosed in either of these disclosures and both methods require extensive work up, namely, isolation and subsequent regeneration of tertiary butyl hydroperoxide from the formed derivatives.

In an effort to satisfy the demand for aqueous solutions of tertiary butyl hydroperoxide exhibiting performance characteristics suitable for use as an intermediate for the production of t-butyl peresters, employable as initiators in polymerization reactions, Borchert et al U.S. Pat. No. 3,773,687 suggests the stabilization of aqueous solutions containing about 60 to 75 weight percent of tertiary butyl hydroperoxide by maintaining the aqueous solution at a temperature of from about 45° C. to about 80° C. for from 0.5 to 10 days. A more recent method for purification of tertiary butyl hydroperoxide described in Worrell et al U.S. Pat. No. 3,864,216 involves azeotropic distillation of diluted isobutane oxidation products from water, which method also employs small quantities of caustic to neutralize carboxylic acids incidental to the oxidation process.

However, all of the aforementioned methods are deficient in providing a tertiary butyl hydroperoxide product having acceptable performance characteristics, as an intermediate for the production of t-butyl peresters, due to the presence of primary and secondary alkyl hydroperoxide contaminants which, in the Worrell et al process, for example, co-distill with the desired tertiary butyl hydroperoxide. Oxygenated derivatives produced from such contaminated t-butyl hydroperoxide product suffer loss in assay and produce deleterious decomposition products which compromise their usage as intermediates in the production of t-butyl peresters, for example, which are useful as polymerization initiators.

Thus, it is a principle object of the present invention to provide an improved process for the purification of tertiary butyl hydroperoxide obtained from isobutane oxidation reaction mixtures.

It is another object of this invention to provide a process for the purification of tertiary butyl hydroperoxide obtained from isobutane oxidation without introduction of additional acidic components.

It is a further object of the present invention to provide a process for the purification of tertiary butyl hydroperoxide obtained from the liquid phase molecular oxygen-containing gas oxidation of isobutane, contaminated with primary and secondary alkyl hydroperoxides.

A still further object of the present invention is to provide a method for preparing tertiary butyl hydroperoxide having improved stability and uniformity, particularly in connection with its use as an intermediate in the production of tertiary butyl perester polymerization initiators.

Further objects will become apparent from the following detailed description and claims.

SUMMARY OF THE INVENTION

In accordance with the present invention, it has been discovered that tertiary butyl hydroperoxide, produced by the oxidation of isobutane with a molecular oxygen-containing gas and contaminated with minor quantities of primary and secondary alkyl hydroperoxides, readily forms salts without significant decomposition when contacted with concentrated solutions of certain inorganic hydroxides, while the primary and secondary alkyl hydroperoxide contaminants are preferentially decomposed by such concentrated aqueous alkali. It has been further found, in accordance with the present invention, that tertiary butyl hydroperoxide is capable of being regenerated from dilute aqueous solutions of its alkali or alkaline earth metal salt without acidification, and may readily be recovered from these salt solutions, for example, by azeotropic distillation at atmospheric pressure, thereby rendering the process of the invention readily adaptable for commercial implementation.

DESCRIPTION OF THE PREFERRED EMBODIMENTS

The present invention is concerned with the process for the purification of tertiary butyl hydroperoxide produced by the oxidation of isobutane with a molecular oxygen-containing gas, and containing minor amounts, generally between about 0.5 and 2 percent by weight, of primary and secondary alkyl hydroperoxides as contaminants, which comprises contacting said tertiary butyl hydroperoxide at a temperature of from about room temperature to about 175° C. with at least about 2 milliequivalents per gram of total hydroperoxide present of a strong aqueous inorganic hydroxide and recovering a tertiary butyl hydroperoxide product containing substantially reduced concentrations of said primary and secondary alkyl hydroperoxide contaminants. The method of selectively decomposing primary and secondary hydroperoxide contaminants contained as undesired impurities in tertiary butyl hydroperoxide by reaction at elevated temperatures with strong inorganic hydroxides is believed to be effected according to the following mechanisms:

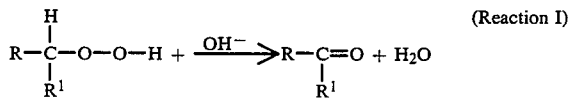

(Reaction I)

wherein $R^1$ is a lower alkyl radical.

A competing reaction involves salt formation by reaction of a strong inorganic hydroxide with a weakly acidic hydroperoxide as illustrated below:

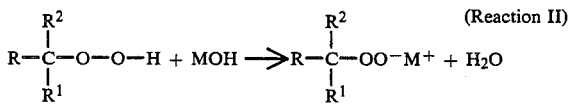

(Reaction II)

wherein $R^1$ and $R^2$ are lower alkyl radicals and M is an alkali or alkaline earth metal. For hydroperoxides other than tertiary alkyl hydroperoxides, Reaction I above is favored at specified elevated temperatures and contact times indicated below, while tertiary hydroperoxides tend to react according to Reaction II above, under the same reaction conditions.

In accordance with the present invention, it has been found that tertiary butyl hydroperoxide readily forms salts without significant decomposition, when reacted with from about 2 to about 10, preferably from about 5 to about 8 milliequivalents per gram of total hydroperoxide present, of a hydroperoxide or oxide of an alkali or an alkaline earth metal, or mixture thereof, in aqueous solution. It has been found that an apparent equilibrium exists between free hydroperoxide and its salts in dilute alkaline solutions, i.e. at tertiary butyl hydroperoxide concentrations of below about 40 percent, as evidenced by the ability to extract repetitively constant quantities of free tertiary butyl hydroperoxide from these solutions with fresh portions of an immiscible organic solvent, illustratively, an aliphatic hydrocarbon such as n-heptane, n-hexane and the like. Distillation of dilute alkaline solutions of these salts results in complete recovery of free tertiary butyl hydroperoxide without decomposition or acidification. In contradistinction, it has been found that primary and secondary hydroperoxide contaminants readily decompose when contacted with such concentrated solutions of hydroxide under the aforementioned conditions. Thus, treatment of tertiary butyl hydroperoxide containing primary and secondary alkyl hydroperoxides as contaminants, in accordance with the process of the present invention, provides an effective means of removing or reducing the concentrations of these contaminants, without destruction of significant quantities of the desired tertiary butyl hydroperoxide product. The realization of such effect by use of alkali or alkaline earth metal hydroxides or oxides at the concentration indicated is indeed surprising, since weaker bases, such as the alkali or alkaline earth metal carbonates or bicarbonates, or organic amines, referred to, for example, in U.K. Pat. No. 1,232,710, fail to achieve such a result.

The tertiary butyl hydroperoxide to be purified in accordance with the process of the present invention is obtained by methods well known in the art, as by vapor or liquid phase oxidation of isobutane with a molecular oxygen-containing gas, as is disclosed, for example, in aforementioned Winkler et al U.S. Pat. No. 2,845,461. The effluent oxidate recovered from the isobutane oxidizer, following distillation of unreacted isobutane therefrom, is comprised, depending upon the reaction conditions employed and degree of conversion of isobutane, of approximately 40 to about 65 percent of tertiary butyl hydroperoxide, between about 30 and 55 percent of tertiary butyl alcohol, and of between about 5 percent and 10 percent, by weight, of other oxidation by-products, including the primary and secondary alkyl hydroperoxide contaminants to be removed in accordance with the process of the invention.

In conventional practice involving the recovery of desired tertiary butyl hydroperoxide product, the isobutane free oxidate is neutralized with base to a pH of about 7 and is subjected to distillation in the presence of a diluent vapor, such as nitrogen. Tertiary butyl alcohol, in the form of water azeotrope, and most oxidation by-product "lights", are recovered as a distillate, and a fraction comprising about 8 to 12 percent, by weight, of tertiary butyl hydroperoxide, contaminated with primary and secondary alkyl hydroperoxides, obtained as the distilland, is continously subjected to further distillation to obtain a tertiary butyl hydroperoxide product overhead as a 65 to 75 percent solution in water, as disclosed in U.S. Pat. No. 3,449,217 and 3,864,216. Although most of the lower boiling oxidation by-products, such as lower alcohols and lower ketones are removed with tertiary butyl alcohol, primary and secondary alkyl hydroperoxides are carried over to tertiary butyl hydroperoxide recovery and remain as impurities with the desired tertiary butyl hydroperoxide product. In general, these primary and secondary alkyl hydroperoxides are present in a concentration ranging from about 0.3 to about 1.2 percent, based on the weight of the isobutane-free oxidate starting material, and from about 0.8 to about 2.8 percent, based on tertiary butyl hydroperoxide present.

The tertiary butyl hydroperoxide solutions employed as starting materials in the process of the present invention may comprise the tertiary butyl hydroperoxide containing oxidate, recovered from the isobutane oxidation following removal, by distillation, of unreacted isobutane, or the tertiary butyl hydroperoxide containing distilland, remaining after distillation of the tertiary butyl alcoholwater azeotrope. Alternatively, the distillate aqueous tertiary butyl hydroperoxide product, containing between about 65 and about 75 percent, by weight, of tertiary butyl hydroperoxide, obtained as a distillate from the distillation of the bottoms fraction of the tertiary butyl alcohol distillation, may serve as starting material in the process of the invention.

Any conventional method of treatment with hydroxide of the tertiary butyl hydroperoxide contaminated with the primary and secondary alkyl hydroperoxides may be employed in the process of the present invention. Especially suitable are the hydroxides of the alkali or the alkaline earth metals, or precursors of any of such basic compounds, such as metal oxides which are capable of forming the hydroxide upon contact with water. Illustrative alkali and alkaline earth metal compounds employable for use in the process of the invention include sodium hydroxide, potassium hydroxide, lithium hydroxide, calcium hydroxide, barium hydroxide, strontium hydroxide, or any alkali or alkaline earth metal oxide which is capable of forming the hydroxide upon contact with water, illustratively, calcium oxide.

The minimum quantity of hydroxide required to form the alkali or the alkaline earth metal salt with tertiary butyl hydroperoxide, while selectively decomposing the primary and secondary alkyl hydroperoxides, is critical for removal or reduction of the primary and secondary alkyl hydroperoxides present as contaminants with the desired tertiary butyl hydroperoxide. In general, the amount of base employed in the process may range from a minimum of about 2 to about 10, preferably between about 5 and about 8 milliequivalents per gram of total hydroperoxide present, and is sufficient to produce a pH of at least about 12, preferably above about 12.5, of the resulting solution. The criticality resides in the employment of a high hydroxide ion concentration which results in selective decomposition of the primary and secondary alkyl hydroperoxid contaminants, which contribute to instability during handling and storage of tertiary butyl hydroperoxide derivatives, such as tertiary butyl peresters.

The exact temperature at which the tertiary butyl hydroperoxide containing the primary and secondary hydroperoxide contaminants is contacted with the hydroxide is not critical, although the rate of decomposition of the contaminants appears to be a function of temperature. In general, the reaction is carried out at a temperature ranging from about room temperature to about 175° C., and preferably between about 60° C. and about 110° C. The time required for contact with the hydroxide should be sufficiently long to permit decomposition of the primary and secondary alkyl hydroperoxide present to a concentration generally below about 0.2 percent, by weight, based on tertiary butyl hydroxide product present as a 70 percent aqueous solution, while at the same time maintaining decomposition of desired tertiary butyl hydroperoxide to a minimum. In general, substantial decomposition of the contaminants may be obtained over the period between about 30 seconds and 2 hours, preferably between about 15 minutes and 1 hour. Under the above stated conditions of temperature and time, decomposition of the desired tertiary butyl hydroperoxide is generally maintained to a minimum, i.e. less than about 20 percent, and generally below about 5 percent.

The purified tertiary butyl hydroperoxide product may be recovered in conventional manner from the alkali or alkaline earth metal salt solutions formed in the process of the invention by liquid-liquid extraction or by azeotropic distillation at atmospheric pressure under a blanket of an inert gas, such as nitrogen. Since the alkali or alkaline earth metal hydroxide is not consumed in the reaction process, except for minimal quantities used to neutralize whatever organic acids present, if any, a particularly advantageous feature of the present process resides in reuse of the hydroxide remaining, following recovery of the tertiary butyl hydroperoxide, as a dilution medium for subsequent contaminant hydroperoxide decomposition. When such spent hydroxide is reemployed in the purification process, the required hydroxide concentration is maintained by the addition of suitable quantities of fresh hydroxide, and recycle optimization may be achieved by maintaining organic acid salt concentration to a minimum.

The following examples are given to further illustrate the invention and to set forth the best mode contemplated of carrying out the invention, but it is to be understood that the invention is not limited by the details described therein.

EXAMPLE 1

Isobutane oxidate solutions containing about 40 percent of tertiary butyl hydroperoxide, about 60 percent of tertiary butyl alcohol, and less than about 5 percent by weight, of oxygenated by-products, including 0.56 percent, by weight (0.8 percent, based on total hydroperoxides present), of primary and secondary alkyl hydroperoxides consisting of isopropyl hydroperoxide, isobutyl hydroperoxide and secondary butyl hydroperoxide are diluted with 5 volumes of water and 20 percent sodium hydroxide such that the caustic concentration is varied at 0.06N and 0.6N. The tertiary butyl alcohol is distilled overhead, leaving an aqueous distilland containing about 10 percent, by weight, of tertiary butyl hydroperoxide contaminated with the above identified primary and secondary alkyl hydroperoxides. A sample of the distilland is heated to a temperature of 80° C. and held at such temperature for a period of 30 minutes. Thereafter, the tertiary butyl hydroperoxide is distilled as an azeotrope, containing about 55 percent of tertiary butyl hydroperoxide, which separates as a two-phase system containing about 70 percent tertiary butyl hydroperoxide in the upper (organic) layer. After neutralization with 5N sulfuric acid to a phenolphthalein end-point, the sample is analyzed by direct injection gas chromatography. The analysis indicates that employment of caustic concentration of 0.8 milliequivalents per gram of total hydroperoxide present results in a reduction of primary and secondary alkyl hydroperoxides to only 0.48 percent, by weight, (0.69 percent, based on total hydroperoxides); in contrast, employment of a caustic concentration of 7.55 milliequivalents per gram of total hydroperoxide present results in reduction of primary and secondary alkyl hydroperoxide contaminants to 0.18 percent, by weight, (0.25 percent, based on total hydroperoxides) with no evidence of significant tertiary butyl hydroperoxide decomposition noted.

This example demonstrates the effect of concentrated caustic on the decomposition of primary and secondary alkyl hydroperoxides, as compared with use of dilute caustic typically employed in prior art procedures for neutralization (U.S. Pat. No. 3,449,217) and removal of formic acid and derivatives (U.K. Pat. No. 1,232,710), without significant decomposition of desired tertiary butyl hydroperoxide.

EXAMPLE II

Samples of the same distilland referred to in Example I above, but containing 0.75, weight percent (0.75 percent, based on total hydroperoxides) of the stated contaminant primary and secondary alkyl hydroperoxides are contacted with sodium hydroxide present in a concentration of 3 milliequivalents per gram of hydroperoxide present at temperatures of 50° C. and 95° C. respectively, over a period of 1 hour. The results indicate reduction of contaminant hydroperoxide concentration, to 0.26 and 0.14 percent by weight, (0.37 and; 0.2 percent, based on total hydroperoxide), respectively, in the final 70 percent tertiary butyl hydroperoxide product.

This Example demonstrates the effect of temperature on the destruction of impurity hydroperoxide concentrations.

EXAMPLE III

A sample of tertiary butyl hydroperoxide obtained as described in Example I above, and containing 0.53 weight percent (0.75 percent based on total hydroperoxides present) of the identified contaminant primary and secondary alkyl hydroperoxides is contacted with sodium hydroxide at a concentration of 3 milliequivalents per gram of total hydroperoxides and at a temperature of 105° C. for a period of 20 minutes. The results indicate reduction of contaminated hydroperoxide concentration, to 0.17 percent, by weight, in the final 70 percent tertiary butyl hydroperoxide (0.24 percent, based on total hydroperoxides), with decomposition of tertiary butyl hydroperoxide initially present of about 10 percent.

EXAMPLE IV

This Example demonstrates the effect of primary and secondary alkyl hydroperoxides on tertiary butyl perester stability.

Tertiary butyl perbenzoate, synthesized in conventional commercial manner from tertiary butyl hydroperoxide containing 0.53 percent, by weight, of the primary and secondary alkyl hydroperoxides identified in Example I, was analyzed and found to contain 0.5 milliequivalents of acid for 100 grams of perbenzoate. Upon storage at room temperature (21° C.), the acidity of the perbenzoate increased to 1.0 milliequivalents of acid after 7 days and further increased to 1.4 milliequivalents after 21 days. Similar increases in acidity are noted with other peresters including, tertiary butyl peracetate and perpivalate, which contain about 0.55 percent, by weight, of the indicated primary and secondary alkyl hydroperoxides.

In contrast, acetate, benzoate and pivalate peresters of tertiary butyl hydroperoxide produced from tertiary butyl hydroperoxide substantially free (i.e. less than 0.2 percent, by weight) of primary and secondary alkyl hydroperoxides analyzed an average of 0.3 milliequivalents of acid per 100 grams of perester, and no increase in acidity is noted after both 7 and 17 days of storage at 21° C. Hence, the presence of primary and secondary alkyl hydroperoxide contaminants with tertiary butyl hydroperoxide, results in relatively high acidity, thereby rendering such contaminated tertiary butyl hydroperoxide unsuitable for the production of commercial quantities of perester polymerization initiators.

We claim:

1. A process for the purification of a tertiary butyl hydroperoxide obtained from the oxidation of isobutane with a molecular oxygen-containing gas and containing minor amounts of undesired primary and secondary alkyl hydroperoxide contaminants, which comprise contacting said tertiary butyl hydroperoxide at a temperature of from about room temperature to about 175° C. for a period of about 30 seconds to about 2 hours with at least 2 milliequivalents per gram of total hydroperoxides present of a hydroxide or oxide of an alkali metal or an alkaline earth metal in aqueous solution and sufficient to produce a pH of about 12 or more of the resulting solution, and recovering said tertiary butyl hydroperoxide containing substantially reduced concentrations of primary and secondary alkyl hydroperoxide contaminants.

2. The process of claim 1 wherein said tertiary butyl hydroperoxide is contacted with said hydroxide or oxide at a temperature of between about 60° C. and 140° C. for a period of between about 15 and 60 minutes.

3. The process of claim 1 wherein said tertiary butyl hydroperoxide is contacted with from about 5 to about 8 milliequivalents per gram of total hydroperoxide present.

4. The process of claim 1 wherein said tertiary butyl hydroperoxide starting material is present as a constituent of an oxidate in an amount of between about 40 and 65 percent, by weight, the remaining constiuents of the oxidate being tertiary butyl alcohol present in an amount between about 30 and 55 percent, by weight, and up to about 10 percent, by weight, of oxidation by-products.

5. The process of claim 1 wherein said tertiary butyl hydroxide starting material is present as an aqueous solution in concentration of between about 8 and 12 percent, by weight.

6. The process of claim 1 wherein said tertiary butyl hydroperoxide starting material is present as an aqueous solution in concentration between about 65 and 75 percent, by weight.

7. The process of claim 1 wherein said hydroxide is sodium hydroxide.

8. The process of claim 1 wherein the tertiary butyl hydroperoxide product is recovered by distillation as a distillate, thereby leaving a spent aqueous hydroxide distilland.

9. The process of claim 8 wherein the spent aqueous hydroxide distilland is recycled to said contacting step for further contact with tertiary butyl hydroperoxide starting material to be purified.

10. A process for the purification of tertiary butyl hydroperoxide containing primary and secondary alkyl hydroperoxide contaminants obtained from the oxidation of isobutane with a molecular oxygen-containing gas which comprises contacting said tertiary butyl hydroperoxide at a temperature of between about 60° C. and about 110° C. for a period of between about 5 minutes and about 2 hours, with from about 5 to 8 milliequivalents of a hydroxide or oxide of an aqueous alkali metal, present in an amount sufficient to produce a pH of at least about 12 and recovering a tertiary butyl hydroperoxide product containing substantially reduced concentrations of said primary and secondary alkyl hydroperoxide contaminants.

11. The process of claim 10 wherein said alkali metal hydroxide is sodium hydroxide.

* * * * *